(12) United States Patent
Schasteen et al.

(10) Patent No.: US 6,750,035 B1
(45) Date of Patent: Jun. 15, 2004

(54) IN VITRO DIGESTIBILITY ASSAY

(75) Inventors: Charles S. Schasteen, St. Louis, MO (US); Jennifer Wu, St. Charles, MO (US)

(73) Assignee: Novus International, Inc., St. Louis, MO (US)

( * ) Notice: Subject to any disclaimer, the term of this patent is extended or adjusted under 35 U.S.C. 154(b) by 19 days.

(21) Appl. No.: 09/633,535

(22) Filed: Aug. 7, 2000

Related U.S. Application Data

(60) Provisional application No. 60/147,571, filed on Aug. 6, 1999.

(51) Int. Cl.[7] .................................................. C12Q 1/37
(52) U.S. Cl. ........................................ 435/23; 426/656
(58) Field of Search .................... 435/23, 176; 424/442; 426/531, 623, 656, 807

(56) References Cited

U.S. PATENT DOCUMENTS

| | | | | |
|---|---|---|---|---|
| 5,518,890 A | * | 5/1996 | Starkweather et al. | ...... 435/7.94 |
| 5,928,686 A | * | 7/1999 | Ivey et al. | ...................... 426/2 |

FOREIGN PATENT DOCUMENTS

| | | | |
|---|---|---|---|
| HU | 155978 | * | 4/1969 |

OTHER PUBLICATIONS

Swainsgood H. Protein Digestibility: In Vitro Methods of Assessment. Advances in Food and Nutrition Research vol. 35, 185–236, 1991.*

Lee E. Trypsin Immobilized on Porous Glass: Preservation and Choice of Reactor. J of Food Science 39(6)1124–1126, 1974.*

Sisak C. Stirred Fluidised Bed Reactor Developed For Low Density Biocatalyst Supports. Biotechnology Techniques 4(1)15–20, 1990.*

Krogh T. Protein Analyis Using Enzymes Immobilized to Paramagnetic Beads. Anal Biochem 274(2)153–162, 1999.*

Porter D. Characterization of an Immobilized Digestive Enzyme System for Determination of Protein Digestibility. J Agric Food Chem vol. 32, 334–339, 1984.*

Buchanan et al., *Interference by Cyanide With The Measurements of Papain Hydrolysis,* Journal of the Science of Food and Agriculture, 1969, vol. 20, pp. 364–367.

Buchanan, *In vivo and in vitro methods of measuring nutritive value of leaf–protein preparations,* The British Journal of Nutrition, Aug. 1969, vol. 23, No. 3, pp. 533–544.

Chang et al., *Protein Digestibility of Alkali– and Fructose–Treated Protein by Rat True Digestibility Assay and by the Immobilized Enzyme Assay System,* J. of Agricultural and Food Chemistry, Apr. 1990, vol. 38, No. 4, pp. 1016–1018.

Chang et al., *Effects of Sucrose, Starch and Oil on the In Vitro Determination of Protein Digestibility Using the Immobilized Digestive Enzyme Assay (IDEA) System,* J. of Food Biochemistry, 1992, vol. 16, No. 3, pp. 133–140.

Church et al., *An o–Phthaladehyde Spectrophotometric Assay for Proteinases,* Analytical Biochemistry, May 1985, vol. 146, No. 2, pp. 343–348.

Culver et al., *Changes in the Digestibility of Dried Casein and Glucose Mixtures Occurring During Storage at Different Temperatures and Water Activities,* J. of Dairy Science, Nov. 1989, vol. 72, No. 11, pp. 2916–2920.

Dudley–Cash, *Methods for determining quality of soybean meal protein important,* Feedstuffs, Jan. 1999, vol. 71, No. 1, pp. 10–11.

Han et al., *Determination of Available Amino Acids and Energy in Alfalfa Meal, Feather Meal, and Poultry By–Product Meal by Various Methods,* Poultry Science, Sep. 1990, vol. 69, pp. 1544–1552.

Jaguelin, et al., *Assessment of the apparent and true N digistibility in pig for several class of feedstuffs through an in vitro determination,* Proc. 6th Int. Symp. Digestive Physiol. in Pigs, 1994, pp. 114–117.

Johnson et al., *Effects on Species Raw Material Source, Ash Content, and Processing Temperature on Amino Acid Digestibility of Animal By–Product Meals by Cecetomized Roosters and Ileally Cannulated Dogs,* J. of Animal Science, vol. 76, No. 4, pp. 1112–1222.

McDonough, *In Vitro Assay for Protein Digestibility: Interlaboratory Study,* Assoc. of Official Analytical Chemistry Journal, Jul.–Aug. 1990, vol. 73, No. 4, pp. 622–625.

Porter et al., *Characterization of an Immobilized Digestive Enzyme System for Determination of Protein Digestibility,* J. of Agricultural and Food Chemistry, Mar.–Apr. 1984, vol. 32, No. 2, pp. 334–339.

Swaisgood et al., *Use of Immobilized Proteinases and Peptidases to Study Structural Changes in Proteins,* Immobilized Enzymes and Cells, 1987, Methods in Enzymology, vol. 135, pp. 596–604.

Swaisgood et al., *Protein Digestibility: In Vitro Methods of Assessment,* Advances in Food and Nutrition Research, 1991, vol. 35, pp. 185–236.

Thresher et al., *Digestibilities of the Protein in various foods as determined in vitro by an immobilized digestive enzyme assay (IDEA),* Plant Foods for Human Nutrition, Mar. 1989, vol. 39, No. 1, pp. 59–65.

Wang et al., *Effect of Raw Material Source, Processing Systems, and Processing Temperatures on Amino Acid Digestibility of Meat and Bone Meals,* Poultry Science, Jun. 1998, vol. 77, No. 6, pp. 834–841.

* cited by examiner

*Primary Examiner*—Ralph Gitomer
(74) *Attorney, Agent, or Firm*—Senniger, Powers, Leavitt & Roedel

(57) ABSTRACT

Methods are provided for determining the digestibility of protein-containing compositions, including food and feed ingredients. The methods comprise incubation of the compositions with proteases, followed by determination of the hydrolyzed peptide bonds. The methods are suitable for rapid, routine determination of digestibility for food and feed processing plants.

74 Claims, 6 Drawing Sheets

IN VITRO DIGESTIBILITY ASSAY

CROSS-REFERENCE TO RELATED APPLICATIONS

This application claims priority from provisional application number 60/147,571, filed Aug. 6, 1999, which is herein incorporated by reference in its entirety for all purposes.

BACKGROUND

1. Field of the Invention

The present invention generally relates to assays to determine the digestibility of protein-containing compositions. More specifically, the present invention relates to in-vitro digestibility assays using proteases.

2. Description of Related Art

The digestibility of protein-containing human food or non-human animal feed can vary greatly. This is particularly true for food or feed ingredients utilized in food or feed processing. Additionally, variations in digestibility can be magnified during processing of these ingredients.

Processing is often performed during production of protein-containing human food or non-human animal feed to make the food or feed more digestible, more nutritious, more preservable, or more palatable. Common processing steps include heating, storing, cooling, drying, wetting, subjecting to pressure, fermenting, particle-size reducing (e.g. by grinding), constituent separating, preservative adding, and mixing of ingredients.

Processing of protein-containing food or feed can affect the digestibility of the food or feed. For example, improper heat or pressure treatment can adversely affect digestibility of vegetable- or animal-based feed and food ingredients (Dudley-Cash, 1999, .Feedstuffs 71:10; Wang et al., 1998, Poultry Sci. 77:834). Also, digestibility of food or feed can be affected by storage conditions (Culver et al. 1998, J Dairy Sci. 72:2916) and the quality of the new raw ingredients (Wang et al., Id).

Digestibility may be measured using in vivo or in vitro assays. See generally Swaisgood et al., 1981, Adv. Food Nutr. Res. 35:185. Several in vivo digestibility assays have been developed, including the rat true digestibility assay (Chang et al., 1990, J. Agric. Food Chem. 38:1016), ileal nitrogen digestibility assays using pigs (Jaguelin et al., 1994, Proc. 6$^{th}$Int. Symp. Digestive Physiol. in Pigs, Bad Dobran, Germany, 114) or dogs (Johnson et al., 1998, J. An. Sci. 76:1112), and precision-fed cockerel assays using conventional or cecectomized animals (Han et al., 1990, Poult. Sci. 69:1544; Wang et al., 1998, Poult. Sci. 77:834). Because these in vivo assays are time consuming, expensive, and difficult to perform, several in vitro digestibility assays have been developed.

In vitro digestibility assays utilize proteolytic enzymes to correlate with in vivo protein digestion. Most of these assays utilize mammalian gastric and/or pancreatic and intestinal enzymes to more closely mimic mammalian digestion. Some assays use one enzyme, usually pepsin, to digest the test protein in solution although papain has also been used (Buchanan, 1969, Br. J. Nutr. 23:533; Buchanan and Byers, J. Sci. Food Agric., 20:364). The digestion is followed by an assay for amino acids. More commonly, the in vitro assays utilize more than one enzyme. Results from these multiple enzyme assays usually correlate more closely to in vivo results than single enzyme assays. Examples of these assays are described in Jaguelin et al., 1994, Proc. 6$^{th}$ Int. Symp. Digestive Physiol. in Pigs, Bad Dobran, Germany, 114 and W, McDonough et al., 1990, J. Assoc. Off. Anal. Chem. 73:622.

A variant of these in vitro enzyme digestibility assays, IDEA (Immobilized Digestive Enzyme Assay), utilizes enzymes which are covalently immobilized on large-pore diameter (200 nm) glass beads via an amide linkage (Porter et al., 1984, J. Agr. Food Chem. 32:334; Chang et al., 1990, J. Agric. Food Chem. 38:1016). By employing immobilized enzymes, this assay has the following advantages over soluble enzyme assays: autolysis (digestion of the enzymes by the enzymes themselves) is prevented, the stability of the enzymes can be increased, the digest is not contaminated with the enzymes or their autolysis products, the digest is easily separated from the enzyme, and the immobilized enzymes can be used in multiple assays. The IDEA method uses two bioreactors. The first contains immobilized pepsin and the second contains immobilized trypsin, chymotrypsin, and intestinal mucosal peptidases. The bioreactors employ either a recirculating design (Chang et al., 1992, J. Food Biochem. 16:133) or a fluidized bed design (Culver et al., 1989, J. Dairy Sci. 72:2916). Digestion of the test sample proceeds in the pepsin bioreactor at low pH (~2) for 18–20 hr at 37° C. The pH of the pepsin digest is then adjusted to 7.5 with $Na_2HPO_4$ then treated with the second biodigester for 24 hr at 37° C. The free a amino groups are then determined using o-phthalaldehyde (OPA) in the presence of mercaptoethanol, which yields adducts which absorb strongly at 340 nm (Church et al., 1985, Anal. Biochem. 146:343). This value is compared the total peptide bonds present in the test sample, determined by complete acid hydrolysis of the sample followed by OPA determination. Digestibility is defined as the fraction of the total peptide bonds present which were hydrolyzed by the digesters.

The IDEA assay has proved useful for digestibility determinations of various complex food compositions (Chang et al., 1990, J. Agric. Food Chem., 38:1016; Thresher et al., 1989, Plant Foods for Hum. Nutr. 39:59; Chang et al., 1992, J. Food Biochem. 16:133). However, the assay takes about two days and requires an elaborate heated recirculation system. Thus, while the IDEA assay is simpler and less costly than the in vivo digestibility assays and has several advantages over the in vitro assays employing soluble enzymes, it is still rather difficult to use for routine determination of digestibility of, e.g., raw materials coming into a processing plant, food or feed at various stages of processing, or finished food or feed. The IDEA system would also be prohibitively time consuming and complex for use in conjunction with animal feed processing; it has not been suggested for that use. Therefore, there is a need for digestibility assays suitable for routine use by, e.g., food and feed processors.

SUMMARY

Among the several aspects of the present invention may be noted the provision of methods for determining the digestibility of food and non-human-animal feed. A more specific aspect of the invention is the provision of such methods in the form of assays which are more rapid and/or simpler to execute than previously known assays. It is also an aspect of the invention to provide digestibility assays wherein the digestibility of a protein-containing composition is determined by visually comparing the assay results with a standard result. A further aspect of the invention is the provision of methods for determining the acceptability of non-human-animal feed ingredients by rapid and simple digestibility assays.

Briefly, therefore, the present invention is directed to a method of measuring digestibility of a protein-containing composition. The method comprises (a) mixing the protein-containing composition with an aqueous liquid to form an aqueous composition; (b) incubating the aqueous composition with a first immobilized protease in a reaction vessel and causing movement of the aqueous composition relative to the immobilized protease in such a manner that none of the aqueous by liquid is removed from the reaction vessel to metabolize a first portion of the protein-containing composition into it, hydrolyzed peptide bonds; and (c) estimating the hydrolyzed peptide bonds.

Another embodiment is directed to a method of measuring digestibility of a protein-containing composition comprising (a) mixing the protein-containing composition with an aqueous liquid to form an aqueous composition; (b) incubating the aqueous composition with a first immobilized protease in a reaction vessel and causing movement of the aqueous composition relative to the immobilized protease in such a manner that none of the aqueous liquid is removed from the reaction vessel to metabolize a first portion of the protein-containing composition into hydrolyzed peptide bonds;(c) separating the composition from the first immobilized protease; (d) incubating the aqueous composition with at least one additional immobilized protease in a reaction vessel and moving the aqueous composition relative to the additional immobilized protease in a generally nonlinear or multidirectional manner; and (e) estimating the hydrolyzed peptide bonds.

The invention is also directed to a method of measuring digestibility of a protein-containing non-human animal feed ingredient. The method comprises (a) mixing the ingredient with an aqueous, acidic liquid to form an aqueous ingredient; (b) incubating the aqueous ingredient at 37° C. with immobilized pepsin in a reaction vessel and causing movement of the aqueous ingredient relative to the immobilized protease in such a manner that none of the aqueous liquid is removed from the reaction vessel to metabolize a first portion of the aqueous ingredient into hydrolyzed peptide bonds; (c) substantially separating the immobilized pepsin from the aqueous ingredient; (d) adjusting the pH of the aqueous ingredient to approximately 7.5; (e) incubating the aqueous ingredient at 37° C. with a mixture of immobilized proteases comprising immobilized trypsin, immobilized chymotrypsin, and immobilized intestinal peptidase in a reaction vessel and causing movement of the aqueous ingredient relative to the immobilized proteases as described in (b) to metabolize a second portion of the aqueous ingredient into hydrolyzed peptide bonds; (f) substantially separating the mixture of immobilized proteases from the aqueous ingredient; and (g) estimating the hydrolyzed peptide bonds in the aqueous ingredient.

Additionally, the present invention is directed to a method of measuring digestibility of a protein-containing composition. The method comprises (a) combining the protein-containing composition with an aqueous liquid to form an aqueous composition; (b) incubating the aqueous composition with a first immobilized protease to metabolize a first portion of the protein-containing composition into free amino groups;.and (c) estimating the free α- and/or ε-amino group concentration by converting the free amino groups into a colored product wherein the intensity of the colored product is proportional to the quantity of converted free amino groups, and comparing the colored product with at least one, colored standard of a particular intensity representing the intensity of color achieved when a particular quantity of free α- and/or ε-amino groups is converted into the colored product.

In another embodiment, the present invention is directed to a kit for measuring digestibility of a protein-containing to composition. The kit comprises (a) a first immobilized An protease; (b) a container for incubating the first immobilized protease with a solubilized protein-containing composition; (c) a reagent for converting free α- and/or ε-amino groups into a colored reaction product; and (d) at least one colored standard of a particular intensity representing the intensity of color achieved when treating a particular quantity of free α- and/or ε-amino groups with the reagent.

The present invention is also directed to a method for determining whether a process increases the digestibility of a protein-containing composition. The method comprises (a) mixing a first portion of the composition with an aqueous, acidic liquid to form an aqueous composition; (b) incubating the aqueous composition at 37° C. with immobilized pepsin in a reaction vessel and causing movement of the aqueous composition relative to the immobilized pepsin in such a manner that none of the aqueous composition is removed from the reaction vessel to metabolize a first portion of the aqueous composition into free amino groups; (c) substantially separating the immobilized pepsin from the aqueous composition; (d) adjusting the pH of the aqueous composition to approximately 7.5; (e) incubating the aqueous composition at 37° C. with a mixture of immobilized proteases comprising immobilized trypsin, immobilized chymotrypsin, and immobilized intestinal peptidase in a reaction vessel and causing movement of the aqueous composition relative to the immobilized proteases in such a manner that none of the aqueous composition is removed from the reaction vessel to metabolize a second portion of the aqueous ingredient into free amino groups; (f) substantially separating the mixture of immobilized proteases from the aqueous ingredient; (g) converting the free α- and/or ε-amino groups into a colored product, wherein the intensity of the colored product is proportional to the quantity of free amino groups; (h) determining the intensity of the colored product; (i) executing the process on a second portion of the composition to form a processed composition; (j) perform steps (a) through (h) on the processed composition; and (k) comparing the intensity of the colored product resulting from performing steps (a) through (h) on the composition with the intensity of the colored product resulting from performing steps (a) through (h) on the processed composition.

In another embodiment, the present invention is directed to a method for determining the digestibility of a protein-containing composition. The method comprises combining the protein-containing composition with an aqueous liquid to form an aqueous composition and then combining the aqueous composition with a thiol protease to form a reaction composition. The reaction composition is then mixed for a sufficient time to hydrolyze the peptide bonds in the protein-containing composition; and the hydrolyzed peptide bonds in the reaction composition determined. In one embodiment, the thiol protease is papain.

Still another embodiment is directed to a kit for measuring the digestibility. The kit comprises a thiol protease, preferably papain, a container for incubating the thiol protease with a solubilized protein-containing composition, and a reagent for converting free amino groups into a colored reaction product. In addition, the kit may contain at least one color standard of a particular intensity representing the intensity of color achieved when treating a particular quantity of free amino groups with the reagent. Optionally, kits of the present invention can also include instructions for using the kits to determine the digestibility of a protein-containing composition, food or non-human animal feed ingredient.

Additionally, the present invention is directed to a method for determining the acceptability of a non-human animal feed ingredient. The method comprises (a) mixing the ingredient with an aqueous, acidic liquid to form an aqueous ingredient; (b) incubating the aqueous ingredient at 37° C. with immobilized pepsin in a reaction vessel and causing movement of the aqueous ingredient relative to the immobilized pepsin in such a manner that none of the aqueous ingredient is removed from the reaction vessel to metabolize a first portion of the aqueous ingredient into free amino groups; (c) substantially separating the immobilized pepsin from the aqueous ingredient; (d) adjusting the pH of the aqueous ingredient to approximately 7.5; (e) incubating the aqueous ingredient at 37° C. with a mixture of immobilized proteases comprising immobilized trypsin, immobilized chymotrypsin, and immobilized intestinal peptidase in a reaction vessel and causing movement of the aqueous ingredient relative to the immobilized proteases in such a manner that none of the aqueous ingredient is removed from the reaction vessel to metabolize a second portion of the aqueous ingredient into free amino groups; (f) substantially separating the mixture of immobilized proteases from the aqueous ingredient; (g) converting,the free $\alpha$- and/or $\epsilon$-amino groups into a colored product, wherein the intensity of the colored product is proportional to the quantity of free amino groups; and (h) comparing the intensity of the colored product to the intensity of a standard, wherein the standard represents the intensity of colored product corresponding to the quantity of free $\alpha$- and/or $\epsilon$-amino groups equivalent to a digestibility value representing a threshold for acceptability of the animal feed composition.

The present invention is also directed to a method for screening-compositions to determine their effect on digestibility of a protein-containing composition. The method comprises, (a) mixing a first portion of the protein-containing composition with an aqueous liquid to form an aqueous composition; (b) incubating the aqueous composition with a first immobilized protease in a reaction vessel to metabolize a first portion of the protein-containing composition into hydrolyzed peptide bonds; (c) moving the aqueous composition relative to the immobilized protease in a generally non-linear or multidirectional manner; (d) estimating the hydrolyzed peptide bonds in the aqueous composition; (e) mixing at least one additional portion of the protein-containing composition with the composition to be screened; (f) repeating (a) through (d) on the additional portion; and (g) comparing the results obtained between said first portion and said additional portion. A further embodiment of this method comprises before (d) incubating the aqueous composition with a second immobilized protease in a reaction vessel and moving the aqueous composition relative to the immobilized protease in a generally nonlinear or multidirectional manner to further metabolize the protein-containing composition into hydrolyzed peptide bonds.

The invention is further directed to a method for screening compositions to determine their effect on digestibility of a protein-containing composition, comprising (a) combining a first portion of the protein-containing composition with an aqueous liquid to form an aqueous composition; (b) combining the aqueous composition with a thiol protease to form a reaction composition, (c) mixing the reaction composition for a time sufficient to hydrolyze the peptide bonds in the protein-containing composition; (d) estimating the hydrolyzed peptide bonds in the reaction composition; (e) combining at least one additional portion of the protein-containing composition with the composition to be screened; (f) repeating (a) through (d) on the additional portion and (g) comparing the results obtained between the first portion and the additional portion.

BRIEF DESCRIPTION OF THE DRAWINGS

These and other features, aspects, and advantages of the present invention will become better understood with regard to the following description, appended claims and accompanying figures where:

DETAILED DESCRIPTION

Figure 1A:
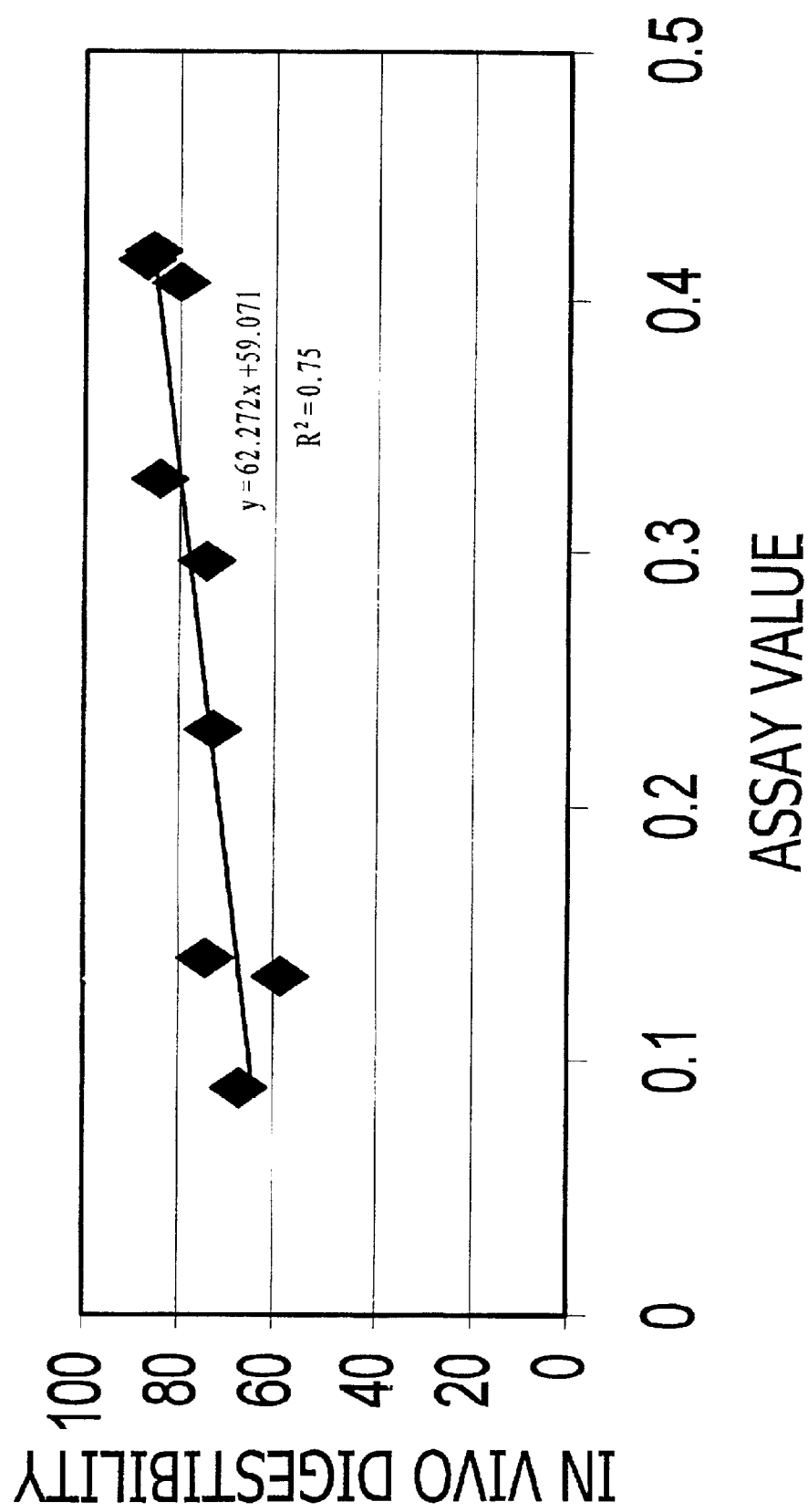
FIG. 1A shows shows the results of regression analysis of values obtained with digestion by immobilized pepsin followed by digestion with a combination of immoblized trypsin, chymotrypsin and intestinal pepdidase using the method of the present invention and True Lys values obtained using in vivo precision-fed cecectomized cockerel assays.
Figure 1B:
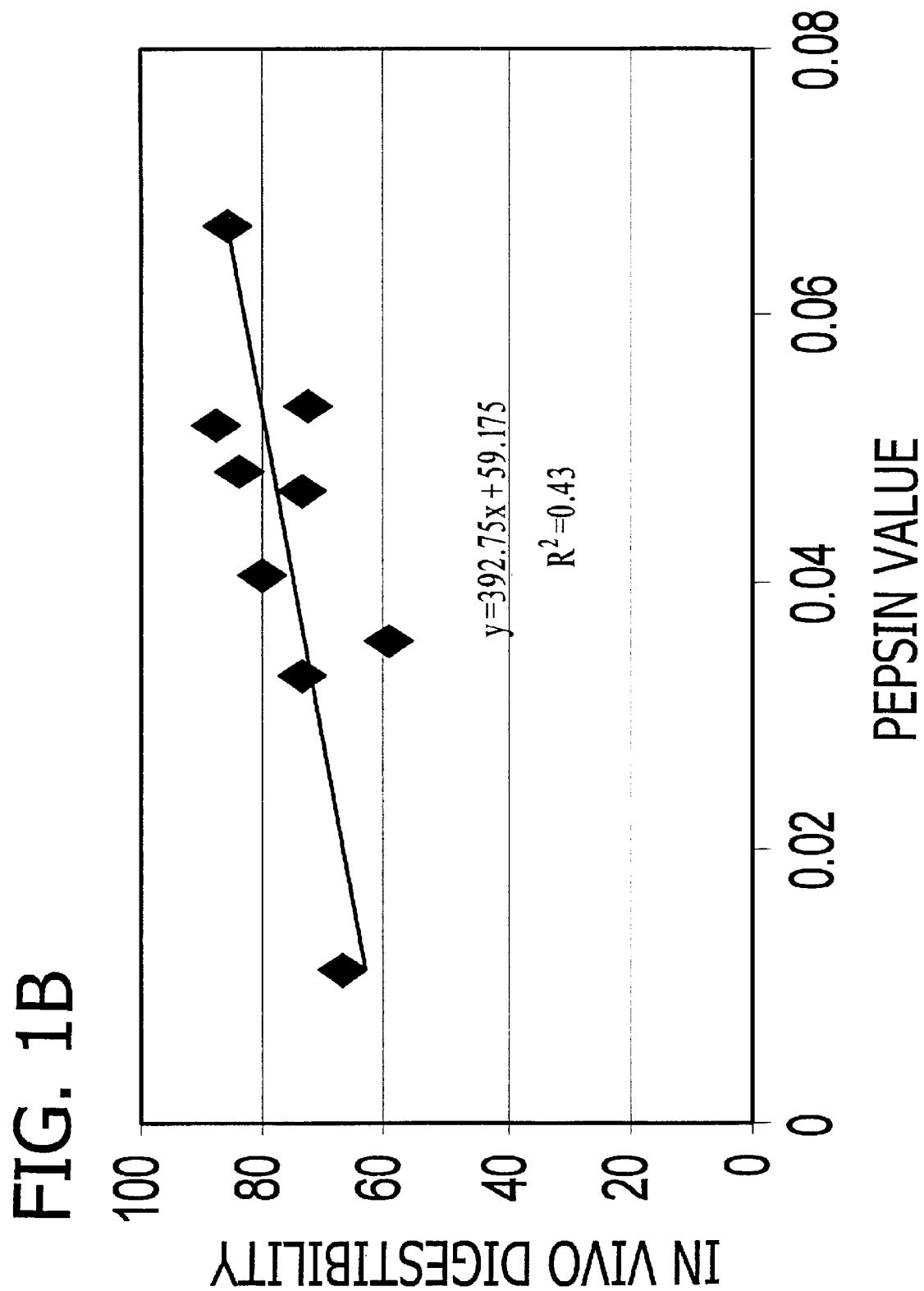
FIG. 1B shows the results of regression analysis of values obtained following digestion of various feeds with immobilized pepsin using the method of the present invention and and True Lys values obtained using in vivo precision-fed cecectomized cockerel assays.
Figure 1C:
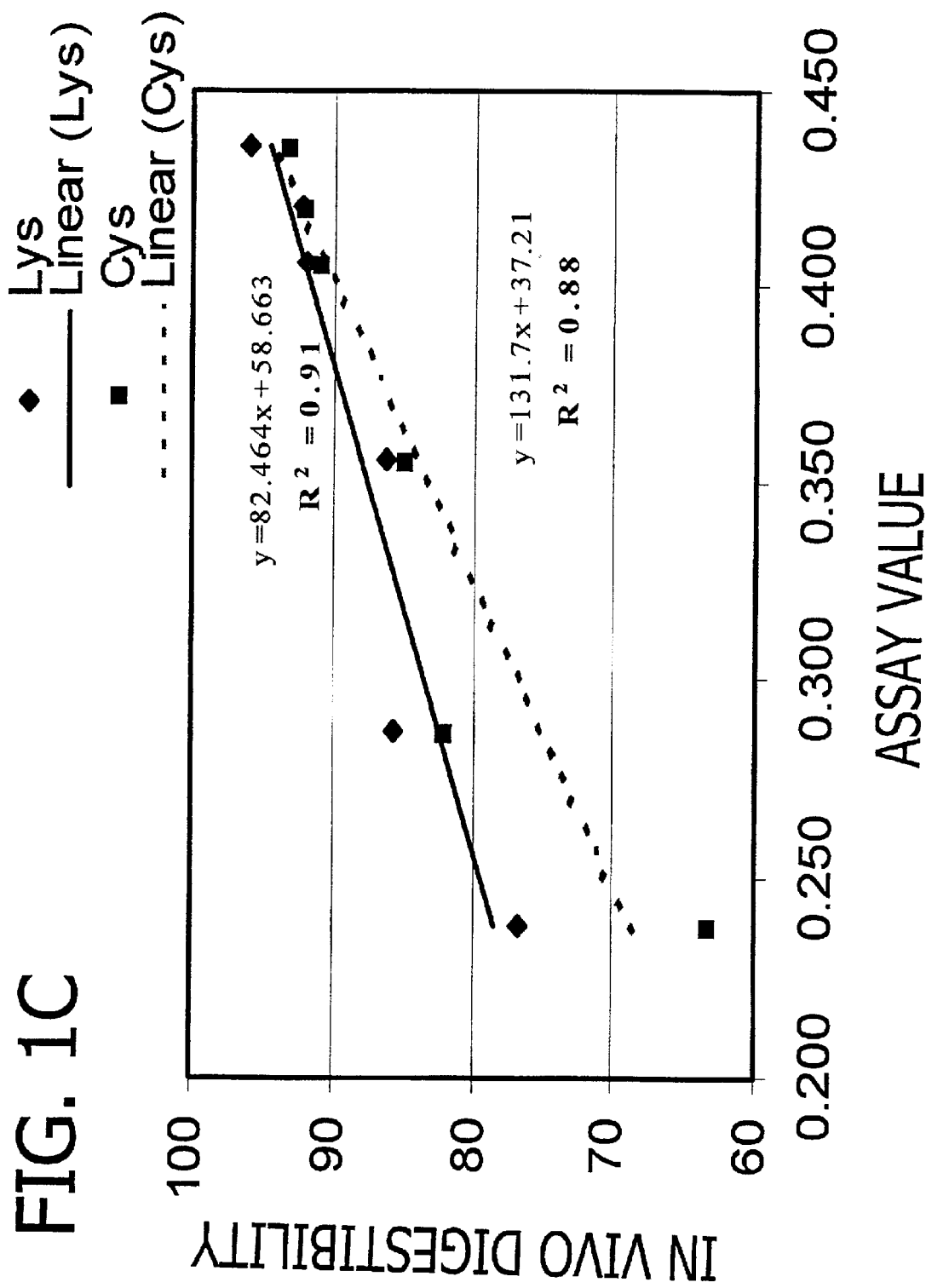
FIG. 1C shows the results of regression analysis of soy flakes determined by the method of the present invention using digestion with immobilized pepsin, followed by immobilized trypsin, chymotrypsin, and intestinal peptidase, and True Lys and True Cys values as determined by the in vivo precision-fed cecectomized cockerel assays.
Figure 1D:
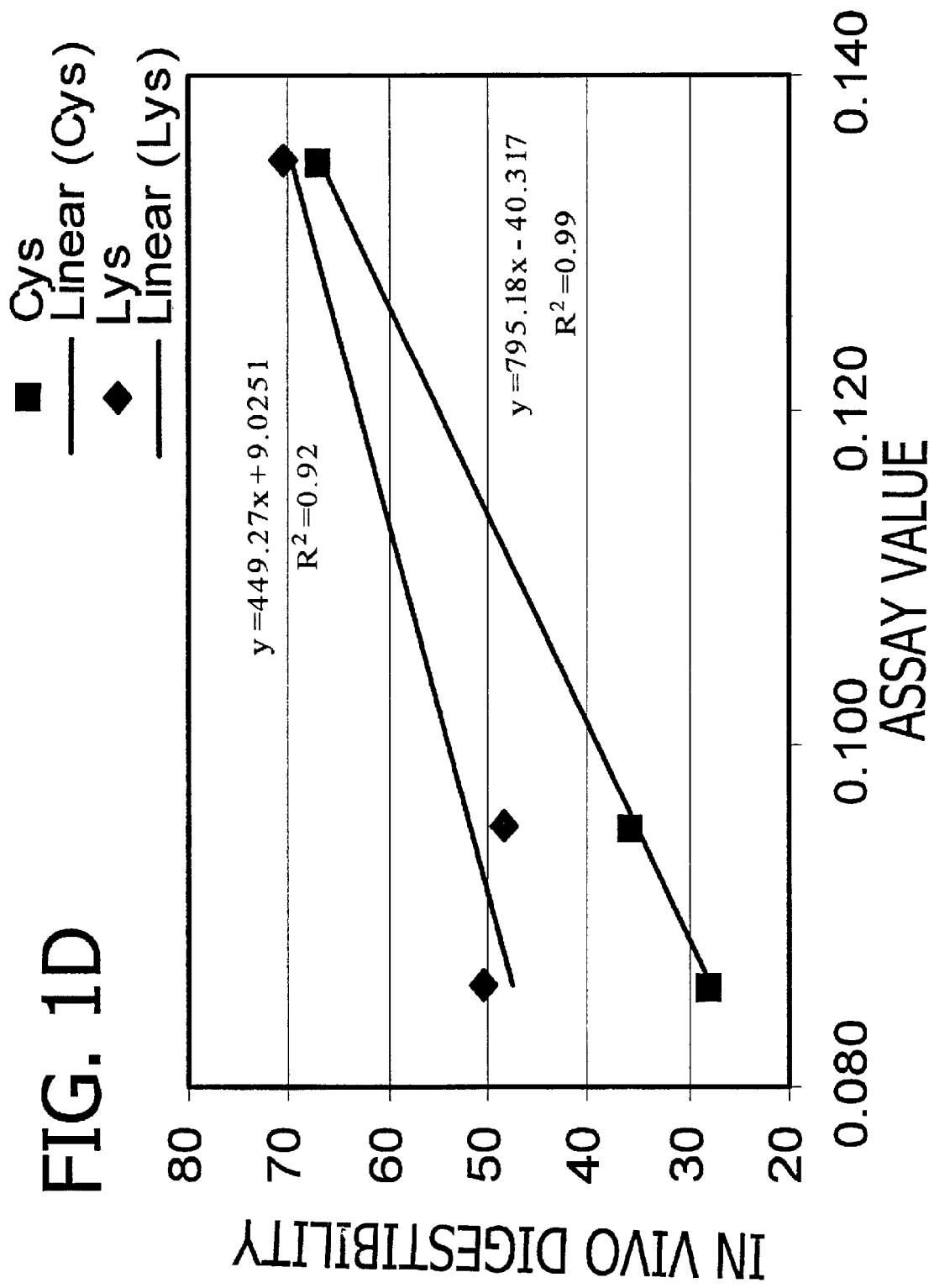
FIG. 1D shows the results of regression analysis of meat and bone meal determined by the method of the present invention using digestion with immobilized pepsin, followed by immobilized trypsin, chymotrypsin, and intestinal peptidase, and True Lys and True Cys values as determined by the in vivo precision-fed cecectomized cockerel assays.

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or swie of the present inventive discovery.

All publications, patents, patent applications and other references cited in this application are herein incorporated by reference in their entirety as if each individual publication, patent, patent application or other reference were specifically and individually indicated to be incorporated by reference.

Abbreviations and Definitions

The listed abbreviations and terms, as used herein, a defined as follows:

MRM=Meat and bone meal
OPA=o-phthaldialdehyde
SDS=Sodium dodecyl sulfate
TNBSA=2,4,6-trinitrobenzenesulfonic acid
TCA=trichloroacetic acid The term "digestibility" is defined herein as the availability of protein for metabolization and utilization of the constituent amino acids by an animal. The digestibility of a protein-containing composition is a function of the amount of protein in the composition and the ability of the digesting animal to metabolize the protein.

The term "food" as used herein means a protein-containing material intended for human dietary consumption. The term "feed" as used herein means a protein-containing material intended for dietary consumption by non-human animals including, but not limited to, pigs, horses, sheep, cows, birds, dogs, cats, and other vertebrates.

The term "metabolize" is used herein to mean an enzymatic process wherein a chemical bond is broken. When the enzyme in the process is a protease, the chemical bond is a peptide bond which is hydrolyzed. The hydrolyzation of a peptide bond results in, among other things, the creation of a free amino group.

When referring herein to an in vitro digestion process, the term "recirculation" is used to mean the continual passage, in an enclosed tube, by the removal of part of the liquid from the reaction vessel and the reintroduction of that liquid to a different part of the reaction vessel. When a digestion process utilizes recirculation, the lipid is tan generally recirculated by a pump through tubing from one end of the reaction vessel to the other end. When the recirculation process removes liquid from the top of the reaction vessel and reintroduces it into the bottom of the to vessel, the digester is referred to as a fluidized bed digester.

The terms "oscillate" or "oscillation" are used herein to mean the movement of an object which varies or fluctuates between fixed limits. The term is intended to embrace any such movements, including shaking, rotating, swinging, bobbing, and rocking movements, but specifically excludes recirculation.

A "protease" is an enzyme which is capable of metabolizing (hydrolyzing) peptide bonds in a protein or an oligopeptide to release individual amino acids or smaller protein or oligopeptide fragments. Examples of proteases are pepsin, trypsin, chymotrypsin, intestinal peptidase, papain and keratinase.

An "immobilized enzyme" is an enzyme which is covalently bound to a larger, insoluble particle.

The terms "percent total protein" "total protein" and "100% digestion value" mean the percent of a composition that is protein and/or peptides.

A "colored product" is a product that has the ability of absorb light at a particular wavelength as determined either by visual examination or by the use of instrumentation such as a spectrophotometer. Thus, the term is not limited to colored products within the visible spectrum, but also includes products which absorb light in the ultra violet and infra red spectra.

The present invention is directed to simplified methods of determining the digestibility of protein-containing compositions. In one embodiment, the method involves in-vitro treatment of the compositions with immobilized proteases followed by an estimation of the extent of digestion of the in compositions by the immobilized proteases.

The protein-containing compositions which are suitable for testing by the methods of the present invention may encompass any protein-containing material which may be used as a human food or a feed for non-human animals. This includes animal or plant-derived homogeneous food or feed ingredients as well as complex food or feed composed of several different ingredients. The compositions may be assayed as a raw material, at any stage of processing, or as a finished food or feed.

The proteases suitable for use in the present invention include any protease which may mimic the digestive processes of the animal for which the protein-containing composition is intended. This may include proteases of bacterial, fungal, plant, or, animal origin. Mammalian proteases are preferred among proteases of animal origin. In one embodiment, the preferred proteases are pepsin, trypsin, chymotrypsin, and intestinal peptidase. In another embodiment, the preferred proteases are thiol proteases and in particular papain.

The proteases may be immobilized on an insoluble matrix which does not appreciably affect the activity of the immobilized protease. Examples of potentially useful matrices are cellulose, agarose, dextran, sephadex, polystyrene, acrylic, silica, and celite. Preferred are glass and magnetic matrices. The matrix should be in the form of particles or beads, preferably approximately 80–200 mesh (approximately 100–150 $\mu$m diameter).

The proteases may be immobilized on the insoluble matrix by any means which will not appreciably affect the protease activity and will not result in appreciable quantities of the protease leaching off the matrix during the assay. Preferred methods result in an active, immobilized protease which can be used in multiple successive assays and can be stored for weeks, more preferably months, or most preferably years. In a preferred method, aminopropyl or, preferably, succinamidopropyl derivatized glass beads are activated with 1-ethyl-3-(3-dimethylaminopropyl) carbodiimide and mixed with the protease (Chang et al., 1992, J. Food Biochem. 16:133; Swaisgood et al., 1987, Meth. Enzymol. 135:596). After preparation, the immobilized proteases can be washed with distilled water and dried by any nondestructive means, for example overnight air drying at 80° C., or by air drying on a filter disk through which vacuum is applied. Alternatively, the immobilized proteases can be stored in a suitable aqueous solution (see, e.g., Porter et al., 1984, J. Agric. Food Chem. 32:334). A preferred aqueous storage solution for pepsin is 0.01 N HCl with 0.1% $NaN_3$, pH 2.0; trypsin, chymotrypsin, and intestinal peptidase is preferably stored in 0.02 M sodium phosphate, 0.1% $NaN_3$, pH 7.5 The immobilized proteases such as pepsin, trypsin, chymotrypsin, or intestinal peptidase retain protease activity for years when prepared using glass beads and the preferred succinamidopropyl derivatization method of. Chang et al., 1992, J. Food Biochem. 16:133, then air dried.

To estimate the digestibility of a protein-containing composition using the assay of the present invention, a sample of the composition is preferably first prepared by grinding the preparation to a fine powder (for example, using a Fritsch Rotor Speed Mill at 20,000 rpm for 20 seconds, to a 1 mm mesh) then combining a portion of the sample with an aqueous liquid to form an aqueous composition. The aqueous liquid is preferably a liquid in which the protease to be utilized is active (i.e., able to hydrolyze peptide bonds). If more than one protease or mixture of proteases is to be used, the aqueous liquid is preferably a liquid in which the first protease to be utilized is active. For example, if the first protease is immobilized pepsin, a preferred aqueous liquid is 0.01 N HCl, pH 2.0. The aqueous liquid preferably also contains a preservative, for example 0.1% sodium azide, to prevent microbial growth during the assay.

The sample is mixed with the aqueous liquid at a concentration of between 0.5 and 300 mg/ml, preferably between 0.5 and 40 mg/ml. In one embodiment the composition has a protein concentration of 2 to 10 mg/ml. Therefore, compositions comprising a high concentration of protein would be mixed at a lower concentration in the aqueous liquid than a composition comprising a low concentration of protein. Examples of preferred concentrations of some components are as follows: ground corn—20 mg solid/ml, 20% protein animal feed—10 mg solid/ml, soybean meal or MBM—4 mg solid/ml. The volume of the aqueous liquid may be 0.1–100 ml, preferably 0.25–15 ml. The volume will, of course, depend on the size of the reaction vessel used. For example, when a 15 ml reaction vessel is used the preferred volume is 2.5 to 7.5 ml. When the smaller 2 ml reaction vessel is used, the sample volume is 0.5 ml. Before the initial mixing with the protease, the aqueous composition may be pre-incubated, for example at room temperature or 37° C., for preferably less than 24 hours in order to solubilize the sample. Surfactants (e.g. Tween 20) or other additives can also be included in the aqueous liquid to promote sample solubilization. However, the sample need not completely dissolve in the aqueous liquid, since the proteases are able to metabolize proteins present on solid sample particles. In one embodiment, the samples are solubilized in 50 mM $H_3PO_4$. In another embodiment, the sample ok is solubilized in 50 mM $KH_2PO_4$.

After mixing (and perhaps incubating) the sample with the aqueous liquid, the aqueous composition is mixed with the protease also in an aqueous liquid. In one embodiment, the fly protease is an immobilized protease. In another embodiment, the protease is a lyophilized thiol protease; In one preferred embodiment, the aqueous composition is directly added to either a protease immobilized to beads, preferably in a liquid, or a lyophilized protease. The quantity of protease used is determined empirically, and can vary depending on the activity of the protease, the size of the sample particles added to the aqueous liquid, whether the aqueous composition is incubated before mixing with the protease, and the conditions and length of time that the aqueous composition is incubated with the protease. Sufficient protease is used whereby the digestion of the aqueous composition is essentially completed or the rate of digestion can be determined when the incubation of the aqueous composition with the protease is terminated. The completion of the digestion can be determined by sampling the aqueous composition at various times during incubation with the protease and determining that there is no further significant increase in metabolic products (e.g. free amino groups) over time. For example, when 5 ml of a 1 mm mesh-ground sample at a concentration of 2 mg/ml is digested, 1.5 ml of pepsin beads, at 4.6 units/g beads, is sufficient when incubated for 18 hr at 37° C. with movement of the aqueous composition relative to the pepsin beads. A preferred first immobilized protease is immobilized pepsin. Another preferred first immobilized protease is a mixture of immobilized trypsin, immobilized chymotrypsin, and immobilized intestinal peptidase. Yet another preferred first protease is papain.

The aqueous composition may be incubated with the protease under any conditions which allow digestion of the aqueous composition. In one embodiment, incubation may be under recirculating conditions, or fluidized bed conditions, for example by the methods of Chang et al., 1992, J. Food Biochem. 16:133 or Culver et al., 1989, J. Dairy Sci. 72:2916, respectively. However, a non-recirculating system is preferred due to its simplicity.

In a non-recirculating system, the immobilized protease is incubated with the aqueous composition in a reaction vessel as the aqueous composition is caused to move relative to the immobilized protease. In a preferred embodiment, the reaction vessel is simply a capped tube or similar structure having a reaction chamber defined by a closed top, a continuous, closed side wall and an end wall, the immobilized protease is fully contained within the reaction chamber and the aqueous composition is caused to move relative to the immobilized protease by oscillation of the vessel for example, by shaking, rotating, swinging, bobbing or rocking the reaction vessel. Moving the reaction vessel in this manner causes multidirectional flow of the aqueous composition past the immobilized protease generally in one linear direction and then in another. Alternatively, the reaction vessel can be moved to induce swirling of the contents, for example, by circular or elliptical movement of the vessel, or it can be held stationary and the aqueous composition may be stirred through the use of stir bars and stir rods to cause the aqueous composition to flow past the immobilized protease in a non-linear direction. Moving the aqueous composition relative to the immobilized protease in any of these manners eliminates the need for sophisticated reaction vessels (e.g., Porter et al., 1984, J. Agri. Food Chem. 32:334; Culver et al., 1989, J. Dairy Sci. 72:2916) which have an opening in the side wall, bottom or top of the reaction chamber for withdrawing the aqueous composition from one position and pumping it to another position of the reaction chamber where it is reintroduced to cause a generally unidirectional linear flow from the reintroduction position, pass the immobilized a protease, and to the withdrawal position. See, e.g., Porter et al., 1984, J. Agri. Food Chem. 32:334; Culver et al., 1989, J. Dairy Sci. 72:2916.

The reaction vessel may be any container which would provide for adequate mixing of the beads with the aqueous composition. With a 5–10 ml incubation volume, a convenient reaction vessel is the 20 ml Bio-Rad (Hercules, California) Econo-Pac column, although smaller 10 and 5 ml columns as well as 2.0 ml microcentrifuge tubes may be used. Additionally, the present invention can be practiced using multi-well plates such a 96 well microtitre plates. Other suitable containers will be readily apparent to those of ordinary skill in the art and are included within the scope of the present invention. Volumes of sample and enzyme used will, of course, vary with the size of the vessel used. For example when using a 10 ml column and a two-step digestion, the first digestion typically contains 7.5 ml of sample combined with 0.75 ml of beads containing immobilized pepsin, while the second digestion contains 5 ml of sample and 1.5 ml of beads containing immobilized trypsin, chymotrypsin and intestinal peptidase. When 2 ml tubes are used in a two step assay, the first digestion typically contains 750 $\mu$l of sample and 150 $\mu$l of beads containing immobilized while the second digestion uses 500 $\mu$l of sample and 150 $\mu$l of beads containing immobilized trypsin, chymotrypsin and intestinal peptidase.

The incubation preferably proceeds at a temperature and pH which is optimal for the protease used. In general, temperatures between 0° and 55° C. are preferred. With pepsin, kit for example, 37° C. is the optimal temperature and 2–3 is the optimal pH. The protease digestion may proceed for 2–24 hours, preferably 4–18 hours. For papain, the optimal temperature and pH are 37° C. and 6.2. When papain is used, the digestion time is preferably 0.5 to 4 hours, more preferably, 2 hours. For trypsin, chymotrypsin, and intestinal peptidase, the optimal temperature and pH are 37° C. and 7.5 and digestion proceeds for 2–24 hours, preferably 18 hours.

After incubation with an immobilized protease, the aqueous composition is preferably separated from the immobilized protease. This separation can be performed by removing the immobilized protease from the reaction vessel, e.g., with a magnet if magnetic particles are utilized as the insoluble matrix. Preferably, however, the separation is performed by removing the aqueous composition from the reaction vessel, e.g., with a pipette or allowing the composition to flow out of the column. When a free protease is used, such as papain, the reaction can be terminated by inactivation of the enzyme for example the addition of an acid, however, this step is not required by the present method.

When multiple digestions are used, after the first digestion (and, if applicable, separation of the aqueous composition from the immobilized protease) the amount of digestion which took place can be determined or, preferably, the aqueous composition is mixed and incubated (as described above) with a second immobilized protease preparation. If the second immobilized protease preparation is not active under the same conditions as the first immobilized protease, the in aqueous composition must be modified (e.g., by adjusting the pH and/or temperature) to accommodate the second immobilized protease preparation.

A preferred second immobilized protease preparation is a mixture of immobilized trypsin, immobilized chymotrypsin, and immobilized intestinal peptidase. These enzymes can be combined to digest the aqueous composition together because they all require similar conditions (optimally, pH 7.5, 37° C.) to be active. Since pepsin (a preferred first immobilized protease) requires a low pH, the pH of the aqueous composition is preferably elevated to 7.5 for example with solid $Na_2HPO_3$ or NaOH between the two protease incubations when using the preferred first and second immobilized proteases. Alternatively, the pH may be adjusted by the addition of a buffer solution, for example, 5M phosphate buffer (4.44M $NaH_2PO_4$, 0.55M $K_2PO_4$) added at the rate of 900 $\mu$l 5M phosphate buffer per 15 ml of pepsin hydrolysate. This second digestion may be incubated for 4–24 hours, preferably 12–24 hours.

If desired, the aqueous composition can further contain a pH indicator for use in adjusting the pH of the aqueous composition for different protease digestions. Various pH indicators will be known to those of ordinary skill in the art and can be used in the practice of the present invention. Examples of suitable pH indicators include phenol red ($C_{19}H_{14}O_5S$) and thymol blue ($C_{27}H_{30}O_5S$). Phenol red detects pH changes between 6.8 (yellow) to 8.2 (red). Thymol blue detects pH changes between 1.2 (red) to 2.8 (yellow) and 8.0 (yellow) to 9.2 (blue).

After all incubations are completed using immobilized proteases, the aqueous composition is preferably separated from the immobilized proteases. Immobilized proteases which were used in the incubations can be regenerated for use in later assays by treating the proteases with a solution suitable for that purpose. For immobilized pepsin, the used is beads are preferably regenerated by washing with 0.01 HCl; a preferred wash treatment for immobilized trypsin, immobilized chymotrypsin, and immobilized intestinal peptidase (or a mixture of the three) is a wash in 2 M urea, followed by a wash in 0.02 M sodium phosphate, 0.28 M NaCl, pH 7.5.

After all protease treatments are completed, the amount of digestion (i.e. peptide bond hydrolysis) is determined by any appropriate means, for example using a microbiological amino acid assay method, automated amino acid analysis, nitrogen analysis, determination of the initial rate of pH drop, or the pH stat method. See, e.g., Swaisgood et al., 1991, Adv. Food Nutr. Res. 35:185 for a discussion of these methods. Since protein hydrolysis by proteases creates a free carboxyl group and a free amino group, preferred methods of determining digestion by a protease involves the measurement of one of these groups. A preferred method of estimating protease hydrolysis is using the o-phthalaldehyde (OPA) method described in Church et al., 1985, Anal. Biochem. 1:343–348, where the absorbance at 340 nm is directly proportional to $\alpha$-amino group concentration. The preferred OPA reagent comprises 80 mg OPA in 2 ml 95% ethanol, 10 ml 10% sodium dodecyl sulfate, 0.2 ml mercaptoethanol, and 50 ml 0.1 M sodium borate, to 100 ml with water. Another preferred method of estimating protease hydrolysis is the TNBSA (2,4,6-trinitrobenzenesulfonic acid) method (Habeeb, 1966, Anal. Biochem. 14:328). TNBSA rapidly reacts with $\alpha$- and $\epsilon$-amino groups to form a chromogenic derivative that can be measured at 420 nm. In this method, 395 $\mu$l of reaction buffer(0.1 M sodium borate, pH 10) is combined with 250 $\mu$l of 0.1% TNBSA in reaction buffer and 5 $\mu$l of sample at a concentration of about 2 mg/ml. The mixture is incubated at room temperature for 10 minutes and the absorbance read at 42.0 nm.

The digestibility of the composition can be determined by comparing the hydrolysis results obtained with the protease with the composition after total hydrolysis, e.g., after hydrolyzing the composition in 6 N HCl for 24 hr at 110° C. For example, when OPA is used, the digestibility is conveniently expressed as $$(A_{340} \text{ final} - A_{340} \text{ initial})/(A_{340} \text{ acid} - A_{340} \text{ initial})$$

where $A_{340}$ is the absorbance of the solution at 340 nm.

Alternatively, the digestibility of the composition can be determined by comparing the hydrolysis results obtained with the protease with total nitrogen content of the starting composition. As is well known in the art, an estimate of the percent protein in a composition can be obtained by multiplying the percent nitrogen by 6.25. The percent nitrogen in the composition can be determined by any method known in the art. In one preferred embodiment the percent nitrogen is determined by a method approved by AOAC International (Official Methods of Analysis of AOAC International, 17 th ed., W. Horwitz ed., AOAC International, 2000). In another preferred embodiment, the percent nitrogen is determined by an automatic nitrogen analyzer such as the Leco N analyzer. In yet another embodiment, the percent nitrogen is determined using the Kjeldahl method.

In order to account for inter assay variation, a control sample can be included in each assay. The control sample consists of a quantity of the same protein-containing composition to be tested for which the digestibility is already known. The control sample is run along with the unknown samples and the digestibility of the control determined. The difference between the known digestibility and the digestibility determined by the assay can be used to obtain a correction factor to standardize the values obtained to the known control.

If a quantitative estimate of digestibility is not required, approximate determinations of digestibility can be conveniently estimated by visually comparing the intensity of the colored product (after treatment of the digested aqueous composition with OPA) with at least one colored standard representing particular degrees of digestion. The colored standard may be a liquid or may simply be a colored solid material such as a card or a piece of paper. This method could be applicable for routine "accept—do not accept" determinations, e.g., where the colored product represents a threshold for acceptability of an ingredient coming into a food or feed processing plant.

The time for the entire digestibility assay of the present invention can be from 0.5 to 72 hours. Preferably, the assay will take 24 hours or less. Parameters affecting the length of time for the assay are sample composition, whether a preincubation is performed on the aqueous sample, the protease used, the activity of the immobilized proteases, the concentration of the aqueous composition, and whether the protease incubations are performed under optimum conditions.

The method of the present invention can also be used to determine whether a particular process increases the digestibility of a protein-containing composition, by determining whether a composition can be digested to a greater extent when using the process than when not using the process. The methods of the present invention can also be used to monitor processing quality and/or effectiveness at each stage of processing a food or feed composition, and approximate the digestibility of a final food or feed product.

The present invention is also useful for screening feed additives and supplements to increase digestibility. In this aspect, the digestibility of a feed is determined by any of the methods of the present invention. The feed is then analyzed again using the same method of the present invention in the presence of the additive or supplement to be screened or following treatment of the feed with the additive or supplement to be screened and any change in digestibility noted.

The present invention also envisions kits for utilizing the methods described herein, where the kits may comprise the proteases, a reaction vessel, a reagent (such as OPA) for determining the amount of digestion occurring as a result of protease treatment, and a colored standard.

EXAMPLES

Example 1

Correlation of In vitro and In vivo Digestibility Determinations of Various Food and Feed Compositions Using Two Protease Digestions Various food and feed ingredients (listed in Table 1) were ground into a fine powder (1 mm mesh) using a Fritsch Rotor Speed Mill at 20,000 rpm for 20 sec. Samples of soy flakes and meat and bone meal listed in Table 2 were processed as follows. Soy flakes were autoclaved at 121° C. and 124 kPa for either 0, 18, 30 or 36 minutes. Meat and bone meal (MBM) was unprocessed (0/0) or processed for 20 minutes at either 45 psi (45/20) or 60 psi (60/20). Soymax is a product of the Owensboro Grain Co., Owensboro, Ky. Samples of the ground ingredients were suspended in 0.01 N HCl, 0.1% $NaN_3$, pH 2.0, to the concentrations indicated in Table 1, then incubated at room temperature for 18 hr to solubilize the ingredients. Each sample was digested as follows. Immobilized pepsin glass beads (1.5 ml at 4.6 units/g beads), prepared by the method of Chang et al., 1992, J. Food Biochem. 16:133, were transferred to an empty 50 ml centrifuge tube. Five ml of the solubilized sample was added to the immobilized pepsin-containing tube, the tube was mixed, the beads allowed to settle by gravity, and the supernatant was discarded. Another 5 ml of the sample was added and the tube was sealed. Samples were mixed on an Orbitron Rotator at 20 orbits per min, at a 23° tilt for 18 hours in a 37° C. incubator. After the pepsin incubation, the beads were allowed to settle and the supernatant (pepsin hydrolysate) was collected. The pH of the pepsin hydrolysate was then adjusted to between 7.25 and 7.75 with solid $Na_2HPO_4$ (about 0.3 g). Immobilized trypsin (0.2 ml at 151 units/g beads), immobilized chymotrypsin (0.3 ml at 50 units/g beads), and immobilized intestinal peptidase (1.0 ml at 0.32 units/g beads), also prepared by the method described in Chang et al. (Id.), were added to an empty 15 ml centrifuge tube. Five ml of the neutralized pepsin hydrolysate was added to the tube, and the supernatant was discarded after mixing. Another 5 ml of the neutralized pepsin hydrolysate was added, the tube sealed and incubated at 37° C. in an Orbitron Rotator as before for 24 hr. The supernatant (final hydrolysate) was collected as above.

Acid hydrolysis of an aliquot of the sample was performed to determine the 100% digestion value of that sample. The amount of the sample needed to make 5 ml of the initial sample solution (see Table 1—e.g. 20 mg sorghum; 100 mg wheat, etc.) was transferred into a 10 ml glass ampule. The sample was dissolved with 5 ml 6 N HCl. The ampule was sealed and heated at 110° C. for 24 hr. The sample was then neutralized with two volumes of 2.5 N NaOH, then filtered through a 0.2 $\mu$m nylon filter (Acrodisc®, Pall Corporation, East Hills, N.Y.).

Determination of α-amino groups in the sample was with OPA. Ten $\mu$l of the initial protein solution, the pepsin hydrolysate, or the final hydrolysate was brought to 1 ml with OPA reagent (80 mg OPA in 2 ml 95% ethanol, 10 ml 10% SDS, 0.2 ml mercaptoethanol, and 50 ml 0.1 M sodium borate, made to 100 ml with water), incubated for two minutes at room temperature, and the absorbance at 340 nm was determined on a Cary 3 spectrophotometer. The OPA reagent served as a blank for the spectrophotometer. The same measurement was made with the acid hydrolysate, then multiplied by 3 to account for the dilution factor. Triplicate measurements were obtained for each sample.

The digestibility of each sample was calculated using the following formula:

$$\text{Assay Value} = (A_{340} \text{ final} - A_{340} \text{ initial})/(A_{340} \text{ acid} - A_{340} \text{ initial})$$

Lysine ("True Lys") and Cysteine ("True Cys") digestibility determinations for most of the samples (Tables 1 and 2) were obtained by the precision-fed cecectomized cockerel assay as described in Wang et al., 1998, Poult. Sci. 77:834. Data from the True Lys in vivo determinations were regressed with the pepsin and final hydrolysate data for the same samples. Although lysine and cysteine were used in the present example, it will be apparent to those in the art that any amino acid can be used for in vivo digestibility determinations.

Data were entered into a Microsoft Excel spreadsheet and a linear regression equation calculated by the least squares method. The $R^2$ value and the equation for the best fit line was generated. The best fit equation was used to determine percent digestibility.

Results are shown in Tables 1 and 2 and FIG. 1. Table 1 shows the final assay values, pepsin values and True Lys and True Cys values for various samples assayed at the concentrations given. Final assay values were obtained by digestion with immobilized pepsin followed by digestion with a combination of immobilized trypsin, chymotrypsin, and intestional peptidase. Pepsin values were obtained by digestion with immobilized pepsin alone.

The results in Table 2 shows the results of determinations of digestibility of soy flakes and meat and bone meal (MBM) after various processing regimes. The soy flakes were autoclaved at 121° C. and 124 kPa for the times given in Table 2. MBM samples were treated for the times and at the pressures given in Table 2 (psi/min). The results show that the methods of the present invention can be used to determine changes in digestibility resulting from processing.

FIG. 1 shows the results of the regression analysis of these data. The data from the final digestion (FIG. 1A) correlated with the in vivo data well ($R^2=0.75$), but the correlation of the pepsin data (FIG. 1B) with the in vivo data was not as strong ($R^2=0.43$). FIG. 1 also shows that the method of the present invention can be used to reflect changes in digestibility resulting from processing as evidenced by the strong correlation between values obtained using the present invention and in vivo values for soyflake (FIG. 1C) and meat and bone meal (FIG. 1D). The strong correlation of the final digestion data with the in vivo data shows that the methods of the present invention is a useful substitute for the in vivo assay.

In an alternative embodiment, the assay was conducted using 10 ml disposable chromatography columns. In this embodiment, the samples were prepared as described above. Immobilized pepsin glass beads (1.5 ml at 4.6 units/g beads) were transferred to a 10 ml column and 7.5 ml of sample added. The column was sealed and incubated on an Orbitron Rotator at 20 orbits per min. at a 23° tilt from 18 hours at 37° C. After the incubation, the pepsin hydrolysate was collected and the pH adjusted to about 7.5 with solid $Na_2HPO_4$. Five ml of neutralized pepsin hydrolysate was added to a 15 ml centrifuge tube containing immobilized trypsin (0.2 ml at 151 units/g beads), immobilized chymotrypsin (0.3 ml at 50 units/g beads) and immobilized intestinal peptidase (1.0 ml at 0.32 units/g beads) and the tube sealed. The tube was then incubated on an Orbitron rotator as above. After incubation, the beads were allowed to settle and the supernatant collected. Acid hydrolysis and determination of α-amino groups were as described above.

TABLE 1

| SAMPLE | FINAL VALUE | PEPSIN VALUE | SAMPLE CONC. | TRUE LYS | TRUE CYS |
|---|---|---|---|---|---|
| Sorgum | 0.1331 | 0.0357 | 4 mg/ml | 59 | 74 |
| Poultry by-product | 0.4206 | 0.0669 | 4 mg/ml | 86 | 86 |
| Wheat | 0.4161 | 0.0519 | 20 mg/ml | 88 | 90 |
| Peanut Meal | 0.4075 | 0.0406 | 4 mg/ml | 80 | 79 |
| Peas | 0.3304 | 0.0484 | 9 mg/ml | 84 | 75 |
| Barley | 0.2979 | 0.0332 | 20 mg/ml | 74 | 82 |
| Sesame | 0.2298 | 0.0533 | 4 mg/ml | 73 | 87 |
| Fish meal | 0.2043 | 0.0551 | 4 mg/ml | 90 | 90 |
| Meat meal | 0.1387 | 0.0468 | 4 mg/ml | 74 | 74 |
| Rice | 0.0887 | 0.0113 | 40 mg/ml | 67 | 79 |

TABLE 2

| SAMPLE | TREATMENT | FINAL VALUE | TRUE LYS | TRUE CYS |
|---|---|---|---|---|
| Soy flakes | 0 min | 0.238 | 76.6 | 63.2 |
| Soy flakes | 18 min | 0.287 | 85.7 | 81.8 |
| Soy flakes | 30 min | 0.356 | 86.2 | 84.8 |
| Soy flakes | 36 min | 0.406 | 92.0 | 90.7 |
| Soymax a | | 0.436 | 96.0 | 93.0 |
| Soymax b | | 0.420 | 92.2 | 92.0 |
| Meat & bone meal | 0/0* | 0.163 | 70.4 | 67.0 |
| Meat & bone meal | 45/20 | 0.108 | 48.2 | 35.8 |
| Meat & bone meal | 60/20 | 0.097 | 50.6 | 27.8 |

*(psi/min)

Example 2

Correlation of In vitro and In vivo Digestibility Determinations of Various Food and Feed Compositions Using a Single Step Combined Protease Digestion Soy bean meal was ground as in Example 1. In addition to the samples, each assay contained a standard control sample whose digestibility was known. Approximately 400 mg of a feed sample was placed into a container and approximately 50 ml of SBM solubilization solution (50 mM $H_3PO_4$, 0.1% w/v $NaN_3$, pH approx. 2.0–2.1) was added resulting in a final sample concentration of about 8 mg/ml. Samples were then continuously stirred using a magnetic stirrer for four hours at room temperature. After the incubation, the pH of the solution was adjusted to approximately 7.5 using 12.5 N NaOH.

Digestion was carried out in 2 ml round bottom microcentrifuge tubes containing a mixture of glass beads to which was immobilized trypsin, chymotrypsin, and intestinal peptidase. The immobilized enzymes were prepared as in Example 1 and the ratio of the three enzymes was the same as in Example 1 except that the total volume of glass beads used was 0.15 ml instead of 1.5 ml. The beads in the tube were allowed to settle, and the fluid containing the beads removed by aspiration. While maintaining constant stirring, 0.5 ml of a the solubilized and neutralized sample was removed from the in container and then added to the digestion tube containing the immobilized enzymes. The centrifuge tube was capped and mixed on a rotator as described in Example 1 for 18 hours at 37° C. At the end of the 18 hour digestion, the beads were allowed to settle, and the supernatant (final hydrolysate) collected.

The 100% digestion value of the sample was determined by either acid hydrolysis or total nitrogen analysis. For acid hydrolysis, the sample and 6 N HCl were added to a glass ampule to give a final sample concentration of 8 mg/ml. The ampules were flame sealed and heated to 110° C. for 24 hours. After 24 hours, the samples were neutralized with 2.5 N NaOH and filtered through 0.2 μm nylon syringe filters. Ten μl of the filtered acid hydrolysis sample was then used for the OPA analysis to determine total protein.

Alternatively, the 100% digestion value was obtained by determining the total N content of the sample using an automatic N analysis system. In this procedure, a percent nitrogen determination for the soybean meal sample was conducted using a Leco nitrogen analyzer following the manufacturer's protocol for determination of percent nitrogen in a feedstuff. Percent protein was estimated by multiplying the percent N by 6.25.

The presence of free α-amino groups was determined in digested samples and acid hydrolysates by OPA analysis. Ten μl of the initial sample solution or 10 μl of the sample after digestion or acid hydrolysis were each added to 1 ml of fresh OPA solution. OPA solution was prepared as described in Example 1.

Figure 2:
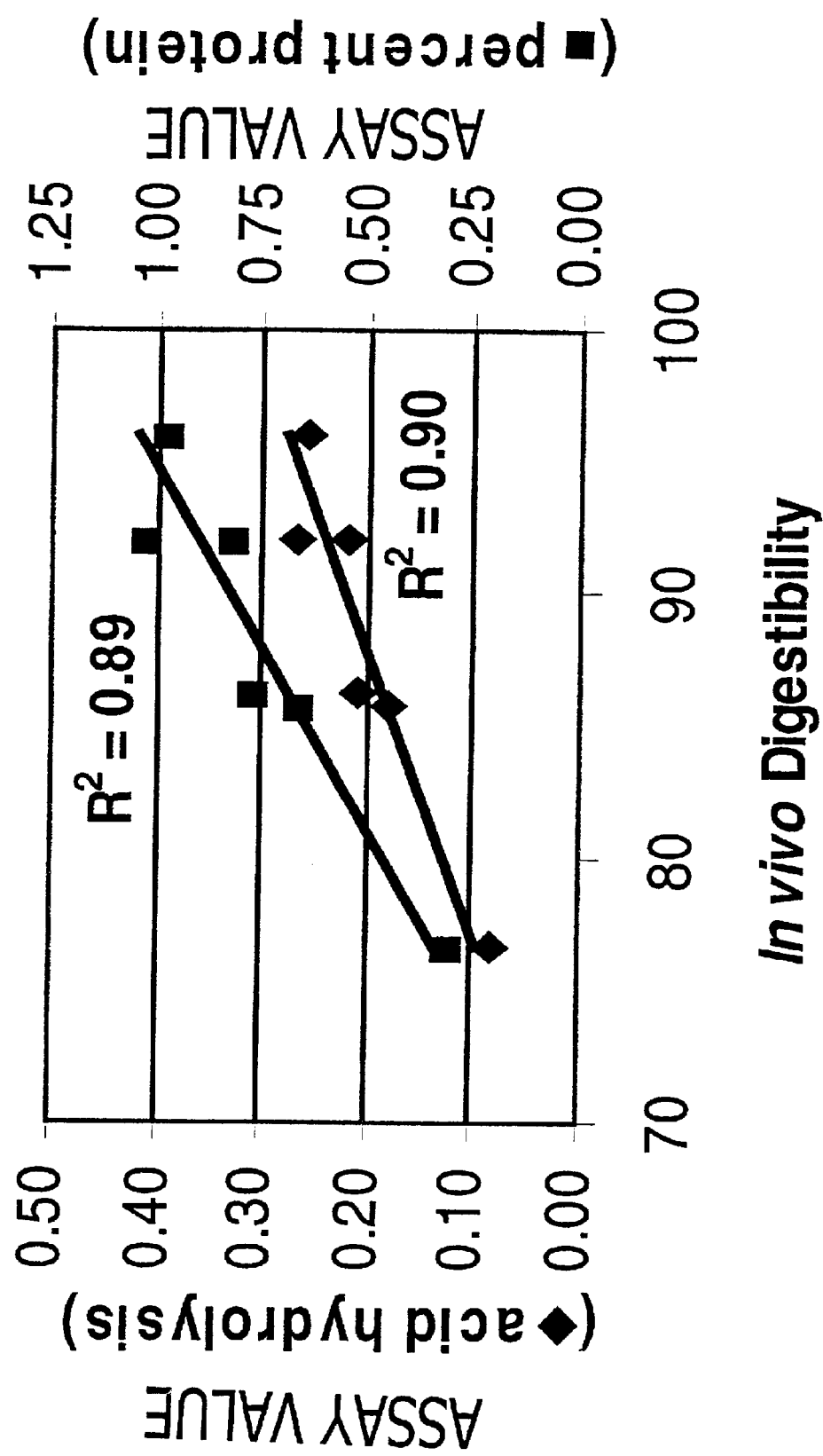
FIG. 2 shows the regression analysis of values obtained following digestion of soy bean meal with immobilized trypsin, chymotrypsin and intestinal peptidase as described in Example 2, and True Lys and True Cys values obtained using in vivo precision-fed cecectomized cockerel assays.

As shown in FIG. 2, there was a high correlation ($R^2$) between the values obtained using the method of the present invention and the True Lys and True Cys values as determined by the in vivo cecectomized cockerel assay.

When acid hydrolysis was used, digestibility was determined using the formula:

assay value=$(A_{340}$ final–$A_{340}$ initial$)/(A_{340}$ acid–$A_{340}$ initial$)$ Assay values obtained were standardize by using the value obtained for the standardized control sample to the known digestibility of the control sample such that:

Corrected value=assay value×standardization factor where the standardization factor was calculated using the formula:

Standardization factor=predetermined assay value (control)/measured assay value (control)

When 100% digestion was determined by N analysis (percent protein), the following formula was used:

assay value=($A_{340}$ final–$A_{340}$ initial)/percent protein

Corrected assay values were obtained as explained above. Once assay values were obtained, percent digestibility was determined by linear regression analysis using regression equations obtained by a comparison of values obtained using the present method and values obtained by in vivo assays as described in Example 1.

Sample calculations using soybean meal are as follows:

$A_{340}$ initial=0.080
$A_{340}$ final=0.489
$A_{340}$ acid=1.908
% protein=50.19

When acid hydrolysis is used the equation is:

is assay value=(0.489−0.080)/(1.908−0.080) =0.224

Predicted digestibility using regression analysis is:

68.5+(97.2×0.224)=90.3

When total nitrogen (percent protein) is used the calculations are as follows:

assay value=0.489−0.080/0.5019=0.815

Using regression analysis, the predicted digestibility is:

69.3+(24.8×0.815)=89.5

Example 3

Correlation of In vitro and In viva Digestibility Determinations of Various Food and Feed Compositions Using a Single Protease Digestion Samples of meat and bone meal (MBM)were ground as described previously. Ground samples were solubilized by placing approximately 400 mg of sample in 50 ml (final conc about 8 mg/ml) of MBM solubilization solution (50 mM $KPO_4$, 0.1% w/v $NaN_3$, 1.2 mM EDTA, 67 μM 2-mercaptoethanol, pH 6.2))and stirred continuously for 15 minutes at room temperature. In addition to the unknown samples, each assay also contained a control sample of MBM used for standardization.

While still stirring the mixture, 2.5 ml of the sample mixture was removed and added to a reaction vial containing 50 units of lyophilized papain. The sample and papain were then mixed on a rotator as described in Example 1 for two hours at 37° C. to produce the final hydrolysate. In some instances the reaction was terminated after 2 hours by addition of 100 μl of 10% trichloracetic acid (TCA), this step, however, is not necessary to practice the assay.

Following digestion, OPA analysis was conducted as described in Example 2 as were acid hydrolysis or percent N determination. Regression equations were determined as described in Example 1.

Figure 3:
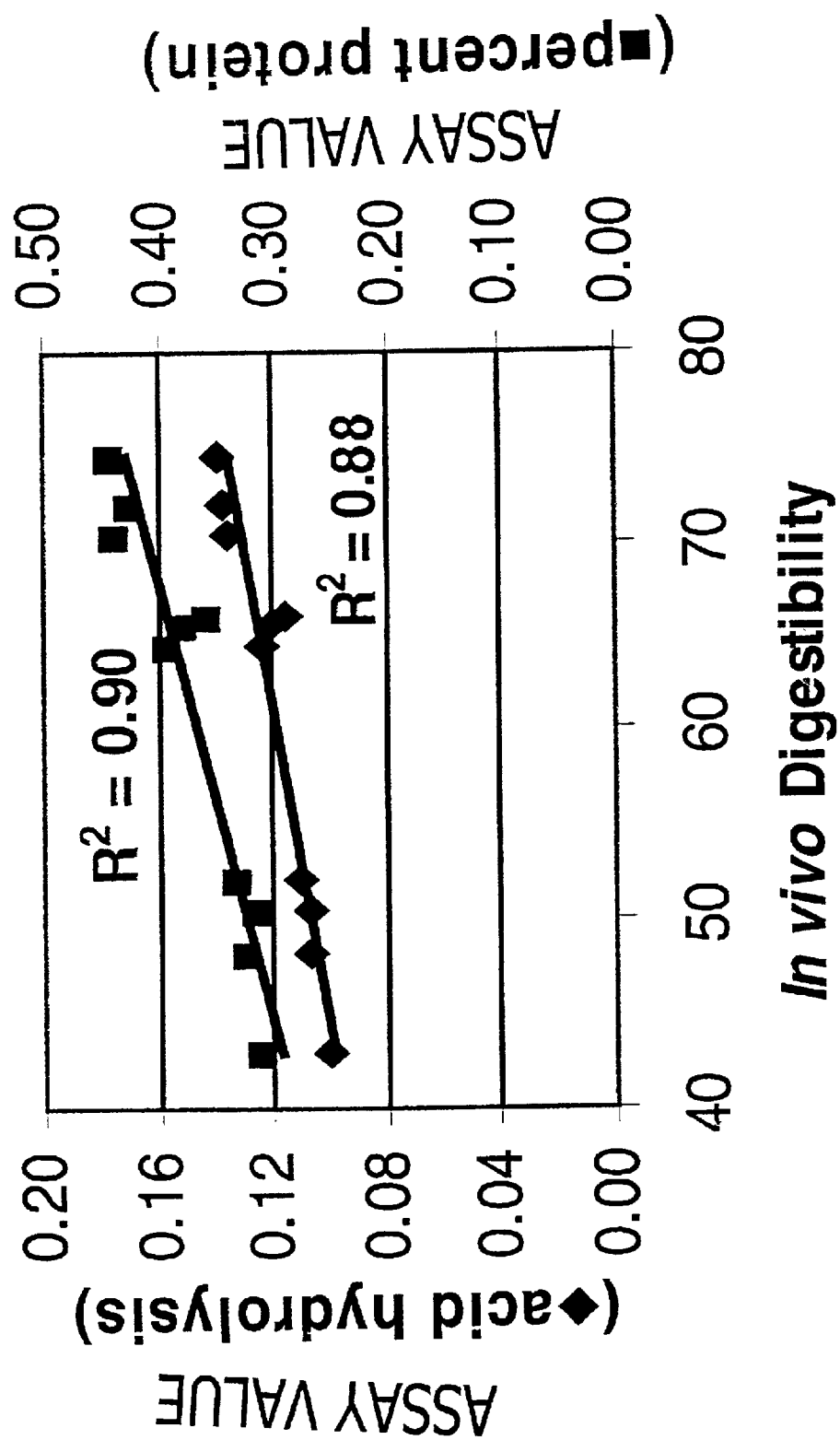
FIG. 3 shows the regression analysis of values obtained following digestion of meat and bone meal with papain as described in Example 3, and True Lys and True Cys values obtained using in vivo precision-fed cecectomized cockerel assays.

As shown in FIG. 3, there was a high correlation ($R^2$) between the values obtained using the method of the present invention and the True Lys and True Cys values as determined by the in vivo cecectomized cockerel assay.

When total nitrogen (percent protein) was used, the assay value was calculated using the formula;

assay value=($A_{340}$final–$A_{340}$ initial–$A_{340}$ background)/percent protein where background is the solubilization solution and enzyme without sample.

When acid hydrolysis was used to determine the 100% digestion values, the assay value was calculated with the following formula:

assay value=($A_{340}$final–$A_{340}$initial–$A_{340}$background)/($A_{340}$acid–$A_{340}$initial)

Values were standardized as described in Example 2.

Sample calculations using meat and bone meal are given below.

$A_{340}$ initial=0.061
$A_{340}$ final=0.344
Enzyme background=0.030
$A_{340}$ acid=1.850
% protein=57.12

When acid hydrolysis is used the equation is:

assay value=(0.344−0.061−0.030)(1.850−0.061)=0.141

The predicted digestibility based on regression analysis is:

(685.0×0.141)−22.1=74.5

When total nitrogen (percent protein) is used the equation is:

assay value=(0.344−0.061−0.030)/0.5712=0.442

Predicted digestibility based on regression analysis is:

(184.7×0.442)−8.6=73.0

CONCLUSION

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventor does not intend to be bound by those conclusions and functions, but puts them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

What is claimed is:

1. A method of measuring digestibility of a protein-containing composition, comprising:
   (a) mixing the protein-containing composition with an aqueous liquid to form an aqueous composition;
   (b) incubating the aqueous composition with a first immobilized protease in a reaction vessel to metabolize a first portion of the protein-containing composition thereby hydrolyzing peptide bonds present in said protein-containing composition;
   (c) moving the aqueous composition relative to the immobilized protease in a generally non-linear or multidirectional manner wherein said moving comprises oscillation of said reaction vessel; and
   (d) measuring the extent of peptide bond hydrolysis in the aqueous composition, said extent of peptide bond hydrolysis constituting a measure of the digestibility of the protein-containing composition.

2. The method of claim 1, wherein the extent of peptide bond hydrolysis in the aqueous composition is measured by comparing the amount of free amino or free carboxyl groups obtained by hydrolysis of said aqueous composition with a measure of the amount of free amino or free carboxyl groups obtainable by total hydrolysis of the protein-containing composition.

3. The method of claim 1, wherein the protein-containing composition is a non-human animal feed ingredient.

4. The method of claim 3, wherein the animal feed is a poultry feed.

5. The method of claim 1 wherein the first immobilized protease is selected from the group consisting of immobilized pepsin, immobilized trypsin, immobilized chymotrypsin, immobilized intestinal peptidase, and a combination thereof.

6. The method of claim 1, wherein the first immobilized protease is immobilized pepsin.

7. The method of claim 1, wherein the first immobilized protease is a mixture of immobilized trypsin, immobilized chymotrypsin, and immobilized intestinal peptidase.

8. The method of claim 1, further comprising, before measuring the extent of peptide bond hydrolysis in the aqueous composition, incubating the aqueous composition with a second immobilized protease in a reaction vessel and moving the aqueous composition relative to the immobilized protease in a generally nonlinear or multidirectional manner to further metabolize said protein-containing composition and effect further hydrolysis of peptide bonds.

9. The method of claim 8, wherein the first immobilized protease is immobilized pepsin.

10. The method of claim 8, wherein the second immobilized protease is selected from the group consisting of immobilized trypsin, immobilized chymotrypsin, and immobilized intestinal peptidase.

11. The method of claim 8, wherein the second immobilized protease is a combination of immobilized trypsin, immobilized chymotrypsin, and immobilized intestinal peptidase.

12. The method of claim 8, wherein the aqueous composition is initially acidic, the first immobilized protease is substantially separated from the aqueous composition after incubating with the immobilized protease, the pH of the aqueous composition is adjusted to approximately 7.5 following separating from first the immobilized protease, but before incubating with the second immobilized protease, and the second immobilized protease is substantially separated from the aqueous composition after incubating with the second immobilized protease.

13. The method of claim 1 or 8, wherein the immobilized proteases are immobilized on glass beads.

14. The method of claim 1 or 8, wherein the immobilized proteases are immobilized on magnetic particles.

15. The method of claim 14, wherein the first immobilized protease and second immobilized protease are separated from the aqueous composition with a magnet after incubating with the aqueous composition.

16. The method of claim 1 or 8, wherein the movement of the aqueous composition is achieved by oscillation, stirring or swirling.

17. The method of claim 1 or 8, further comprising a pre-incubation of the aqueous composition before incubating with the immobilized protease.

18. The method of claim 1 or 8, wherein the extent of peptide bond hydrolysis in the aqueous composition is measured by converting free amino groups into a colored product wherein the intensity of the colored product is proportional to the quantity of converted free amino groups.

19. The method of claim 18, wherein the free amino groups are converted into the colored product by reacting the free amino groups with o-phthalaldehyde or 2,4,6,-trinitrobenzenesulfonic acid.

20. The method of claim 18, wherein the concentration of free amino groups is further estimated by visually comparing the colored product with at least one colored standard of a particular intensity representing the intensity of color achieved when a particular quantity of free amino groups are converted into the colored product.

21. The method of claim 1 or 8 wherein the extent of peptide bond hydrolysis is measured by comparing the amount of peptide bonds hydrolyzed in said aqueous composition with an estimate of the percent protein in the protein-containing composition.

22. The method of claim 21, wherein the percent protein is estimated by determining the percent nitrogen in the protein-containing composition and multiplying the percent nitrogen by 6.25.

23. The method of claim 1 or 8 wherein the method takes from about 0.5 hours to about 24 hours.

24. A method as set forth in claim 1, wherein said reaction vessel comprises a tube having a reaction chamber defined by a closed top, a continuous dosed side wall and an end wall, wherein said tube is closed by a cap.

25. A method as set forth in claim 1, wherein said reaction vessel comprises a non-circulating reaction vessel.

26. A method as set forth in claim 1, wherein said method occurs in about 24 hours.

27. A method as set forth in claim 1, wherein said method occurs in about 2 hours.

28. A method of measuring digestibility of a protein-containing non-human animal feed ingredient, comprising:
   (a) mixing the ingredient with an aqueous, acidic liquid to form an aqueous ingredient;
   (b) incubating the aqueous ingredient at 37° C. with immobilized pepsin in a reaction vessel to metabolize the aqueous ingredient, thereby hydrolyzing a portion of the peptide bonds present in said aqueous ingredient;
   (c) moving the aqueous ingredient relative to the immobilized pepsin in a generally non-linear or multidirectional manner wherein said moving comprises oscillation of said reaction vessel;
   (d) substantially separating the immobilized pepsin from the aqueous ingredient;
   (e) adjusting the pH of the aqueous ingredient to approximately 7.5;

(f) incubating the aqueous ingredient at 37° C. with a mixture of immobilized proteases comprising immobilized trypsin, immobilized chymotrypsin, and immobilized intestinal peptidase in a reaction vessel to further metabolize the aqueous ingredient, thereby hydrolyzing at least a portion of the peptide bonds remaining in said aqueous ingredient after incubating with immobilized pepsin;

(g) moving the aqueous ingredient relative to the immobilized proteases in a generally non-linear or multidirectional manner wherein said moving comprises oscillation of said reaction vessel;

(h) substantially separating the mixture of immobilized proteases from the aqueous ingredient; and (i) measuring the extent of peptide bond hydrolysis in the aqueous ingredient, said extent of peptide bond hydrolysis constituting a measure of the digestibility of the protein-containing ingredient.

29. The method of claim 28, wherein movement of the aqueous ingredient is achieved by oscillation, swirling or stirring.

30. The method of claim 28, wherein the immobilized pepsin, immobilized trypsin, immobilized chymotrypsin, and immobilized intestinal peptidase are immobilized on glass beads.

31. The method of claim 28, wherein the immobilized pepsin, immobilized trypsin, immobilized chymotrypsin, and immobilized intestinal peptidase are immobilized on magnetic particles.

32. The method of claim 31, wherein the immobilized pepsin and mixture of immobilized proteases are separated from the aqueous ingredient with a magnet.

33. The method of claim 28, wherein the extent of peptide bond hydrolysis in the aqueous ingredient is measured by converting free amino groups into a colored product wherein the intensity of the colored product is proportional to the quantity of free amino groups.

34. The method of claim 33, wherein the free amino groups are converted into the colored product by reacting the free amino groups with a phthalaldehyde or 2,4,6-trinitrobenzenesulfonic acid.

35. The method of claim 33, wherein the concentration of free amino groups is estimated by visually comparing the colored product with at least one colored standard of a particular intensity representing the intensity of color achieved when a particular quantity of free amino groups are converted into the colored product.

36. The method of claim 23, wherein the extent of peptide bond hydrolysis is measured by comparing the amount of peptide bonds hydrolyzed in said aqueous ingredient with an estimate of the percent protein in the protein-containing ingredient.

37. The method of claim 28 wherein the extent of peptide bond hydrolysis is measured by comparing the amount of free amino or free carboxyl groups obtained by hydrolysis of said aqueous ingredient with a measure of the amount of free amino or free carboxyl groups obtainable by total hydrolysis of the protein-containing ingredient.

38. The method of claim 28, wherein said protein-containing ingredient is an ingredient of unknown digestibility, the method further comprising:

measuring the digestibility of a control sample of known digestibility, and comparing the measure of digestibility of the known sample with the measure of digestibility of the protein-containing ingredient of unknown digestibility, thereby standardizing the measure of the digestibility of the protein-containing ingredient.

39. A method as set forth in claim 38 wherein measuring the digestibility of the control sample comprises:

mixing said sample with an aqueous liquid to form an aqueous sample composition;

incubating the aqueous sample composition with a thiol protease or a first immobilized protease in a reaction vessel to metabolize a first portion of the sample, thereby hydrolyzing peptide bonds present in said sample;

moving the aqueous sample composition relative to the immobilized protease in a generally non-linear or multidirectional manner wherein said moving comprises oscillation of said reaction vessel; and measuring the extent of peptide bond hydrolysis in the aqueous sample composition, said extent of peptide bond hydrolysis constituting a measure of the digestibility of the sample.

40. The method of claim 38 further comprising:

comparing the measure of digestibility of said control sample with its known digestibility to provide a correction factor; and applying said correction factor to the measure of digestibility of the protein-containing ingredient, thereby standardizing the measure of digestibility of the protein-containing ingredient.

41. The method of claim 40 wherein said correction factor is the ratio of the known digestibility of the control sample to the measure of digestibility of the control sample.

42. The method of claim 28 wherein the extent of peptide bond hydrolysis is measured by comparing the amount of peptide bonds hydrolyzed in said aqueous ingredient with a measure of the amount of peptide bonds hydrolyzed after total hydrolysis of the protein-containing ingredient.

43. The method of claim 42, wherein said total hydrolysis comprises contacting a sample of said protein-containing ingredient with 6 N HCL from about 18 to about 30 hours at a temperature comprising from about 100° C. to about 120° C.

44. The method of claim 43, wherein said total hydrolysis comprises contacting said sample with 6 N HCL for about 24 hours at a temperature of about 110° C.

45. A method of measuring digestibility of a protein-containing composition, comprising:

(a) mixing the protein-containing composition with an aqueous liquid to form an aqueous composition;

(b) incubating the aqueous composition with a first immobilized protease to metabolize the protein-containing composition; thereby releasing free amino groups from protein contained in the composition; and (c) measuring digestibility by measuring the concentration of said free amino groups after incubating, wherein measuring said concentration of said free amino groups comprising converting the free amino groups into a colored product wherein the color intensity of the colored product is proportional to the concentration of free amino groups, and visually comparing the colored product with at least one colored standard of a particular intensity representing known digestibility wherein the intensity of color achieved on said colored standard represents a particular concentration of free amino groups converted into the colored product.

46. The method of claim 45, wherein the protein-containing composition is a non-human animal feed ingredient.

47. The method of claim 45, further comprising, before measuring the free amino group concentration, incubating the aqueous composition with a second immobilized protease in the reaction vessel to further metabolize the protein-containing composition to yield a composition comprising additional free amino groups released from protein contained in said aqueous composition.

48. The method of claim 47, wherein the first immobilized protease is immobilized pepsin and the second immobilized protease is a combination of immobilized trypsin, immobilized chymotrypsin, and immobilized intestinal peptidase.

49. The method of claim 48, wherein the aqueous composition is initially acidic, the immobilized pepsin is substantially separated from the aqueous composition after incubating with the immobilized pepsin, and the pH of the aqueous composition is adjusted to approximately 7.5 following separating from the immobilized pepsin but before incubating with the second immobilized protease.

50. The method of claim 47, wherein the first immobilized protease and second immobilized protease are immobilized on glass beads.

51. The method of claim 47, wherein the first immobilized protease and second immobilized protease are immobilized on magnetic particles.

52. The method of claim 51, wherein the first immobilized protease and second immobilized protease are separated from the aqueous composition with a magnet after incubating with the aqueous composition.

53. The method of claim 45, further comprising a pre-incubation of the aqueous composition before incubating with an immobilized protease.

54. The method of claim 45, wherein the incubating comprises a fluidized bed process.

55. The method of claim 45, wherein the incubating comprises a recirculating process.

56. The method of claim 45, further comprising during the incubating, moving the aqueous composition relative to the immobilized protease in a generally non-linear or multidirectional manner.

57. The method of claim 45, further comprising estimating the total protein content of the protein-containing composition and estimating the percent digestibility of the protein-containing composition.

58. A method for measuring the digestibility of a protein containing composition, comprising:
  (a) combining the protein-containing composition with an aqueous liquid to form an aqueous composition;
  (b) combining said aqueous composition with a thiol protease to form a reaction composition;
  (c) mixing the reaction composition at a temperature of less than 55° C. for a time sufficient to hydrolyze peptide bonds present in said protein-containing composition; and
  (d) measuring the extent of peptide bond hydrolysis in the aqueous composition said extent of peptide bond hydrolysis constituting a measure of the digestibility of the protein-containing composition.

59. The method of claim 58, wherein the thiol protease is papain.

60. The method of claim 45, wherein the extent of peptide bond hydrolysis in the aqueous composition is measured by converting free amino groups into a colored product wherein the intensity of the colored product is proportional to the quantity of free amino groups.

61. The method of claim 60, wherein the free amino groups are converted into a colored product by reacting the free amino groups with o-phthaldehyde or 2,4,6-trinitrobenzenesulfonic acid.

62. The method of claim 60, wherein the concentration of free amino groups is further estimated by visually comparing the colored product with at least one colored standard of a particular intensity representing the intensity of color achieved when a particular quantity of free amino groups are converted into the colored product.

63. The method of claim 58, wherein the extent of peptide bond hydrolysis is measured by comparing the amount of peptide bonds hydrolyzed in said aqueous composition with an estimate of the percent protein in the protein-contain composition.

64. The method of claim 36 or 63 wherein the percent protein is estimated by determining the percent nitrogen in the protein-containing composition and multiplying the percent nitrogen by 6.25.

65. The method of claim 58, wherein the method takes 4 hours or less.

66. The method of claim 58 wherein the extent of peptide bond hydrolysis is measured by comparing the amount of peptide bonds hydrolyzed in said aqueous composition with a measure of the amount of peptide bonds hydrolyzed after total hydrolysis of the protein-containing composition.

67. The method of claim 66, wherein said total hydrolysis comprises contacting a sample of said protein-containing composition with 6 N HCL from about 18 to about 30 hours at a temperature comprising from about 100° to about 120° C.

68. The method of claim 67, wherein said total hydrolysis comprises contacting said sample with 6 N HCL for about 24 hours at a temperature of about 110° C.

69. The method of claim 58 wherein the extent of peptide bond hydrolysis is measured by comparing the amount of free amino or free carboxyl groups obtained by hydrolysis of said aqueous composition with a measure of the amount of free amino or free carboxyl groups obtainable by total hydrolysis of the protein-containing composition.

70. The method of claim 1 or 58 wherein said protein-containing composition is a composition of unknown digestibility, the method further comprising:
  measuring the digestibility of a control sample of known digestibility; and
  comparing the measure of digestibility of the known sample with the measure of digestibility of the protein-containing composition of unknown digestibility, thereby standardizing the measure of the digestibility of the protein-containing composition.

71. A method as set forth in claim 70 wherein measuring the digestibility of the control sample comprises:
  mixing said sample with an aqueous liquid to form an aqueous sample composition;
  incubating the aqueous sample composition with a thiol protease or a first immobilized protease in a reaction vessel to metabolize a first portion of the sample, thereby hydrolyzing peptide bonds present in said sample;
  moving the aqueous sample composition relative to the immobilized protease in a generally non-linear or multidirectional manner wherein said moving comprises oscillation of said reaction vessel; and
  measuring the extent of peptide bond hydrolysis in the aqueous sample composition, said extent of peptide bond hydrolysis constituting a measure of the digestibility of the sample.

72. The method of claim 70 further comprising:
  comparing the measure of digestibility of said control sample with its known digestibility to provide a correction factor; and
  applying said correction factor to the measure of digestibility of the protein-containing composition, thereby standardizing the measure of digestibility of the protein-containing composition.

73. The method of claim 72 wherein said correction factor is the ratio of the known digestibility of the control sample to the measure of digestibility of the control sample.

74. The method of claim 43, wherein said total hydrolysis comprises contacting said sample with 6 N HCL for about 24 hours at a temperature of about 110° C.

* * * * *

UNITED STATES PATENT AND TRADEMARK OFFICE
CERTIFICATE OF CORRECTION

PATENT NO. : 6,750,035 B1
DATED : June 15, 2004
INVENTOR(S) : Charles S. Schasteen et al.

It is certified that error appears in the above-identified patent and that said Letters Patent is hereby corrected as shown below:

Column 20,
Line 43, "dosed side" should read -- closed side --.

Column 21,
Line 40, "a phthalaldehyde" should read -- o-phthalaldehyde --.
Line 48, "method of claim 23" should read -- method of claim 28 --.

Column 23,
Line 57, "method of claim 45" should read -- method of claim 58 --.

Column 24,
Line 8, "protein-contain" should read -- protein-containing --.
Line 15, "method of claim 58" should read -- method of claim 1 or 58 --.
Line 23, "100°" should read -- 100°C --.

Column 26,
Lines 1-3, this claim should not have been entered.

Signed and Sealed this

Twenty-fourth Day of May, 2005

JON W. DUDAS
*Director of the United States Patent and Trademark Office*